(12) United States Patent
Murphy et al.

(10) Patent No.: US 8,579,115 B2
(45) Date of Patent: Nov. 12, 2013

(54) PROTECTIVE CONTAINERS FOR MEDICAL DEVICES AND METHODS OF USE

(75) Inventors: Christopher Murphy, Vass, NC (US); Corey Russ, Fayetteville, NC (US)

(73) Assignee: Combat Medical Systems, LLC, Fayetteville, NC (US)

( * ) Notice: Subject to any disclaimer, the term of this patent is extended or adjusted under 35 U.S.C. 154(b) by 47 days.

(21) Appl. No.: 12/869,614

(22) Filed: Aug. 26, 2010

(65) Prior Publication Data
US 2012/0051967 A1    Mar. 1, 2012

(51) Int. Cl.
*B65D 85/20*    (2006.01)
(52) U.S. Cl.
USPC .......................... 206/364; 206/363; 206/365
(58) Field of Classification Search
USPC .............................. 422/28; 206/363, 364, 365
See application file for complete search history.

(56) References Cited

U.S. PATENT DOCUMENTS

| | | | |
|---|---|---|---|
| 333,347 A | 12/1885 | Schrader | |
| 422,450 A | 3/1890 | Ross | |
| 426,400 A | 4/1890 | Tagliabue | |
| 1,007,804 A | 11/1911 | Schimmel | |
| 1,280,687 A | 10/1918 | Dudley | |
| 1,667,248 A | 4/1928 | Eisele | |
| 1,803,825 A | 5/1931 | Abernathy | |
| 1,838,825 A | 12/1931 | Goldstein | |
| 2,023,289 A | 12/1935 | Pringle | |
| 2,298,938 A * | 10/1942 | Griffin, Jr. et al. | ............ 220/373 |
| 2,400,722 A | 5/1946 | Swan | |
| 2,695,744 A | 11/1954 | Gattuso | |
| 2,935,228 A | 5/1960 | Cosby, Jr. et al. | |
| 3,114,455 A | 12/1963 | Claisse et al. | |
| 3,149,717 A * | 9/1964 | Castelli | ........................ 206/365 |
| 3,318,289 A | 5/1967 | Marynissen | |
| 3,329,146 A | 7/1967 | Waldman, Jr. | |
| 3,342,319 A * | 9/1967 | Faulseit | ........................ 206/365 |
| 3,434,587 A * | 3/1969 | Ciampa | ........................ 206/365 |
| D230,403 S | 2/1974 | Englund | |
| 3,934,722 A | 1/1976 | Goldberg | |
| 4,106,622 A | 8/1978 | Windischman | |
| 4,113,090 A | 9/1978 | Carstens | |
| 4,154,342 A * | 5/1979 | Wallace | ........................ 206/439 |
| 4,444,355 A | 4/1984 | Cary | |
| 4,592,744 A | 6/1986 | Jagger et al. | |
| 4,704,254 A * | 11/1987 | Nichols | ........................ 422/28 |
| 4,757,381 A | 7/1988 | Cooper et al. | |
| 4,877,132 A | 10/1989 | Makris et al. | |
| 4,921,096 A * | 5/1990 | McFarlane | .................... 206/349 |
| 4,954,239 A | 9/1990 | Mueller | |
| D313,245 S | 12/1990 | Iwase | |
| D321,472 S | 11/1991 | Evans et al. | |
| D323,529 S | 1/1992 | Rousseau | |
| 5,090,564 A | 2/1992 | Chimienti | |
| D324,543 S | 3/1992 | Poisson | |
| 5,161,681 A | 11/1992 | Kemp et al. | |

(Continued)

*Primary Examiner* — Sean E Conley
(74) *Attorney, Agent, or Firm* — Knobbe, Martens, Olson & Bear, LLP

(57) ABSTRACT

A container having a base and a cap is disclosed herein for protecting needles and/or catheters during transport. The base has a cavity for storing the needle and/or catheter and a flange region for securing the needle and/or catheter within the base. The cap can be releasably coupled to the base and provide a seal to protect the needle and/or catheter from contamination. Semi-permeable plugs can be disposed on the ends of the base and cap to enable gas sterilization of the container and the needle and/or catheter contained inside.

20 Claims, 11 Drawing Sheets

(56) References Cited

U.S. PATENT DOCUMENTS

| | | |
|---|---|---|
| 5,332,092 A | 7/1994 | Fischer |
| 5,417,326 A | 5/1995 | Winer |
| D362,269 S | 9/1995 | Hollington |
| D366,902 S | 2/1996 | Takahashi |
| 5,641,947 A | 6/1997 | Riddle, Jr. |
| 5,765,682 A | 6/1998 | Bley et al. |
| 5,950,827 A | 9/1999 | Odom et al. |
| 6,155,420 A | 12/2000 | Phillips |
| 6,305,541 B1 | 10/2001 | Tanner et al. |
| D454,394 S | 3/2002 | Jansen |
| 6,488,149 B1 | 12/2002 | Montagnino |
| 6,595,362 B2 * | 7/2003 | Penney et al. .......... 206/364 |
| D488,864 S | 4/2004 | Fago et al. |
| 6,749,601 B2 | 6/2004 | Chin |
| 6,837,400 B2 * | 1/2005 | Leoncavallo et al. .... 222/189.09 |
| D584,408 S | 1/2009 | Castellani |
| D584,409 S | 1/2009 | Miller et al. |
| D584,410 S | 1/2009 | Miller et al. |
| D595,847 S | 7/2009 | Miller et al. |
| 7,874,426 B2 | 1/2011 | Castellani |
| 2003/0121812 A1 | 7/2003 | Sprieck et al. |
| 2003/0125678 A1 | 7/2003 | Swenson et al. |
| 2003/0183545 A1 | 10/2003 | Lauryssen et al. |
| 2007/0232978 A1 | 10/2007 | Castellani |
| 2008/0173556 A1 | 7/2008 | Castellani |
| 2009/0148941 A1 * | 6/2009 | Florez et al. .................. 435/325 |

* cited by examiner

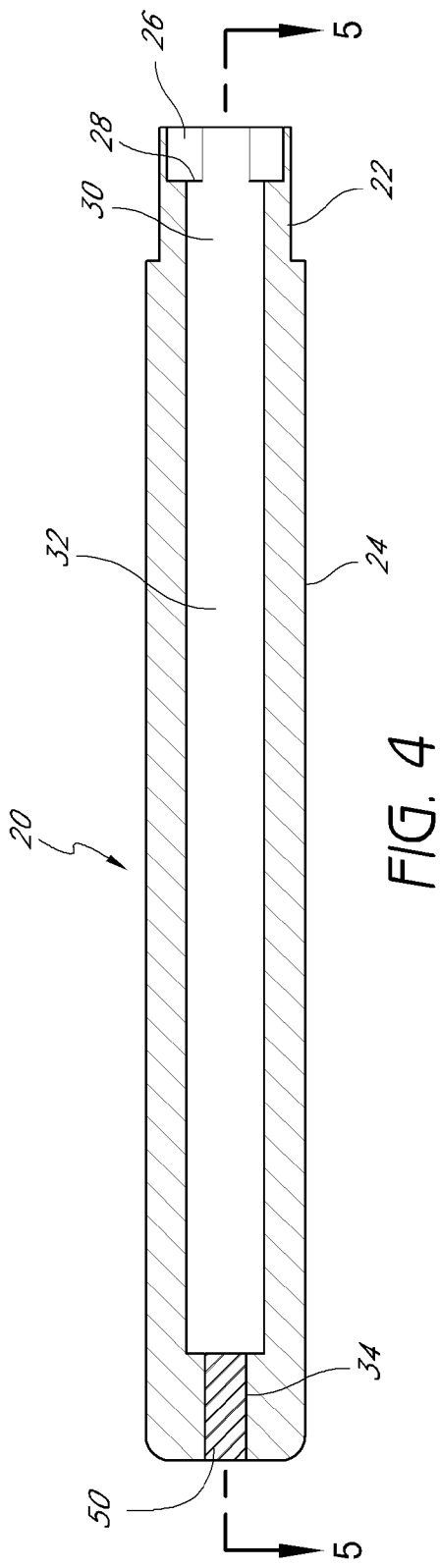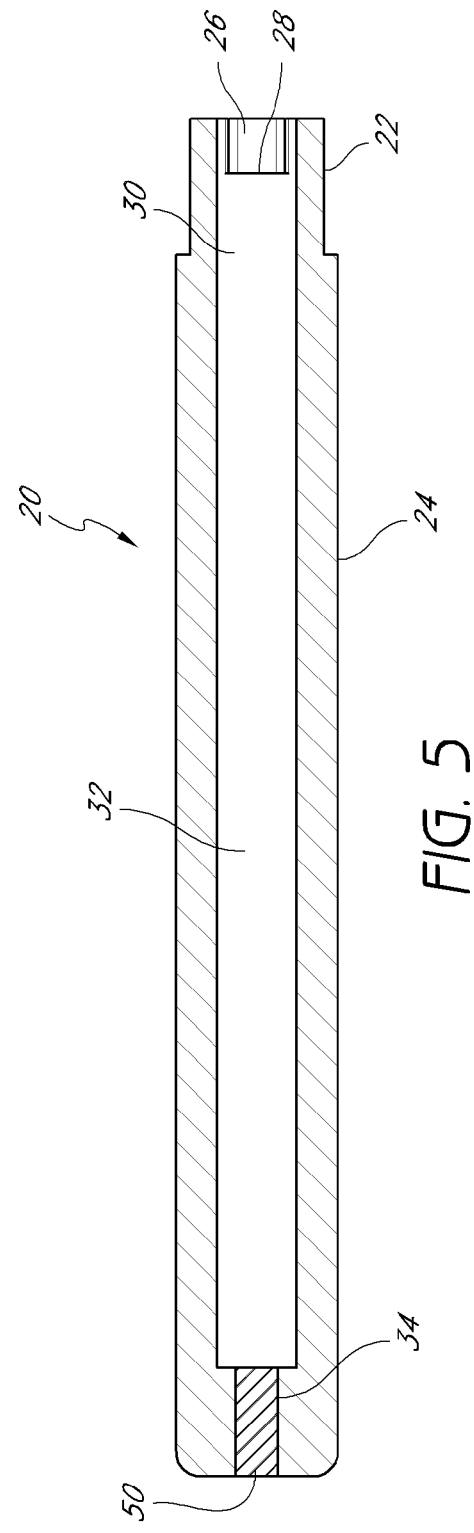

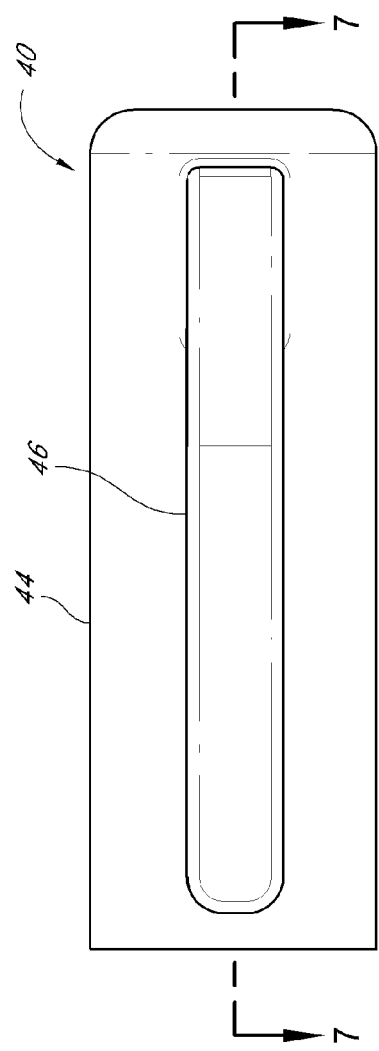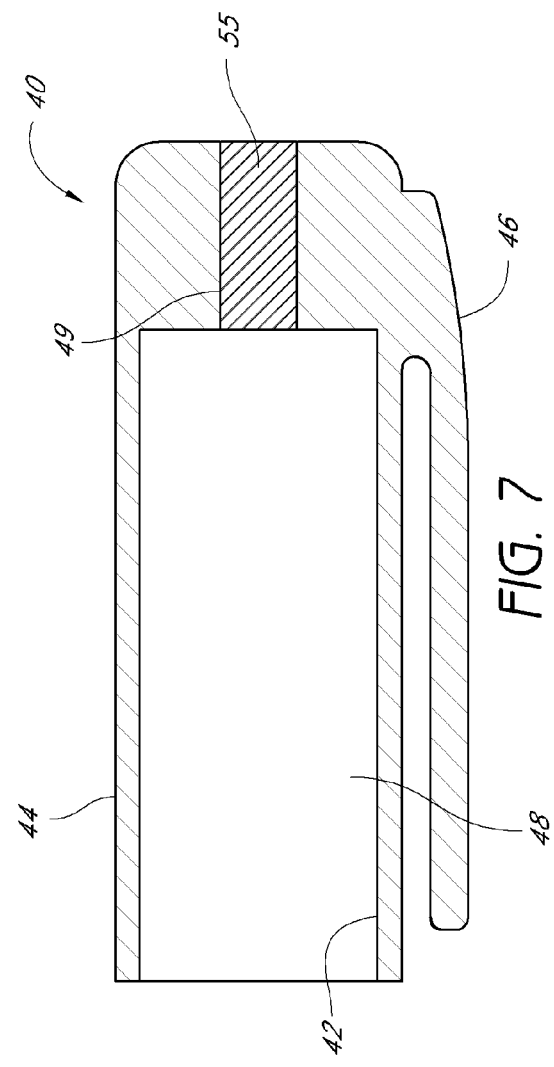

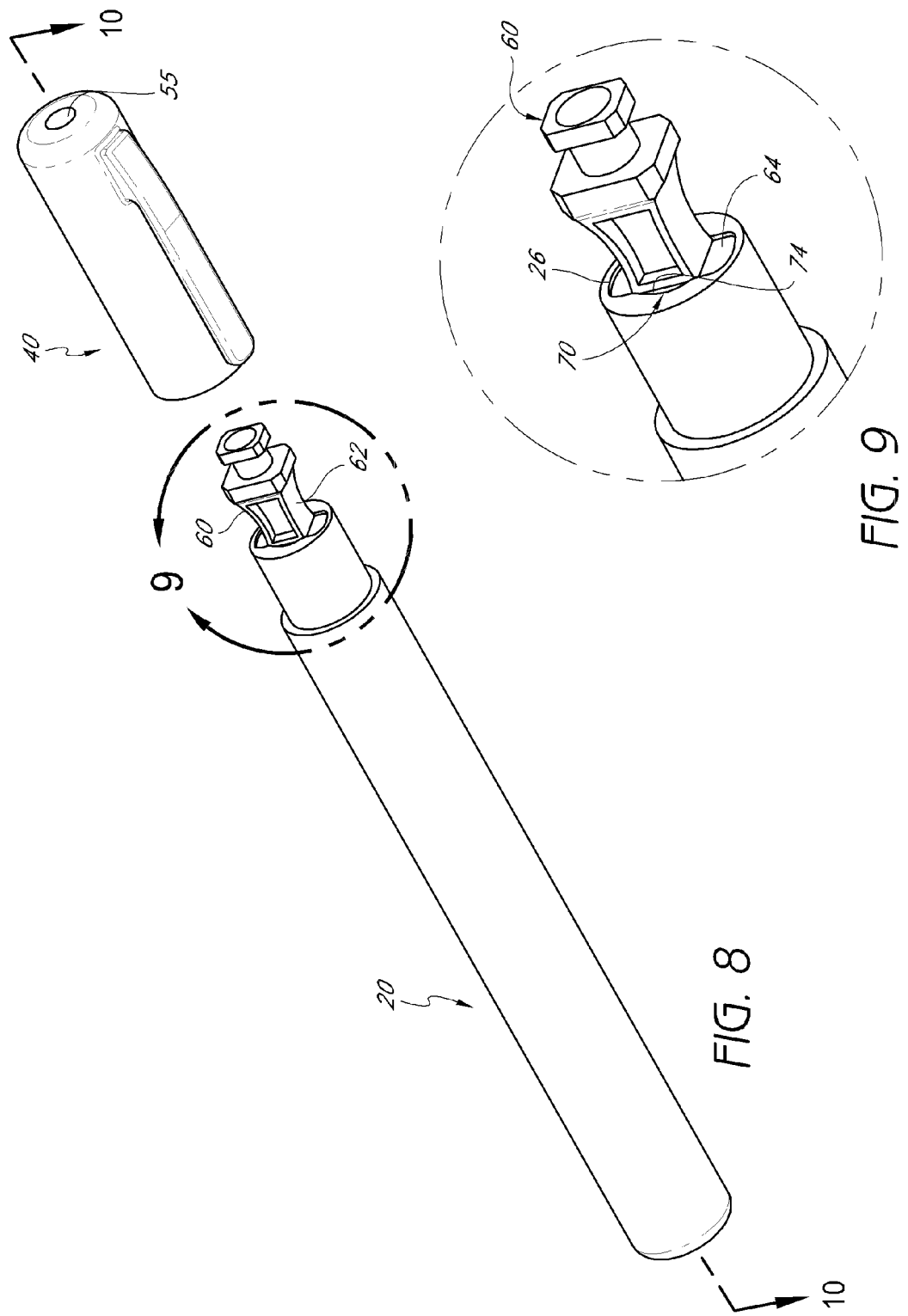

PROTECTIVE CONTAINERS FOR MEDICAL DEVICES AND METHODS OF USE

BACKGROUND

1. Field

This disclosure relates generally to the field of containers and specifically to containers that hold and protect medical devices, such as needles and/or catheters, for transport and storage.

2. Description of Related Art

Medical devices often require special care when stored and transported prior to use. In some situations, the devices can cause damage or injury if accidentally brought into contact with a person, such as when a medical needle inadvertently pierces someone's skin. In addition, medical devices are often fragile and can be damaged easily if not protected. Moreover, in many situations, medical devices must be exposed to a sterilization procedure during the manufacturing process and then must be maintained in a sterile environment until used. These factors present challenges to those who manufacture, transport, and use medical devices. These challenges can be especially difficult in fast-paced, urgent-care medical settings, such as in emergency facilities in hospitals, on the battlefield, and in civil first-responder situations.

For example, in military settings, military medics often carry backpack type medical kits made of durable cloth-like materials that contain various essential items for dealing with life threatening wounds. These soft kits are often subject to severe stresses associated with the rigors of warfare, where the individual carrying the soft kit is often running along walls, diving on the ground, and generally engaging in rigorous physical activity that impact the items in the kit. Furthermore, these soft kits are often carried through dirty or contaminated environments by the military medics, such as through rivers, mud, etc.

Among the various items included in these soft medical kits are various needles and catheters, such as those used for administering intravenous fluid. Some kits can include decompression hypodermic needles intended for use in the management of combat casualties who present signs and symptoms of tension pneumothorax.

Often, such needles and catheters come packaged in a flexible paper and plastic wrapper that does little to protect the contents inside from physical impacts and other stresses. In some circumstances, the devices may even poke through the paper packaging and thereby lose sterility or even cause personal injury.

SUMMARY OF THE DISCLOSURE

In some embodiments disclosed herein, medical device containers are provided that protect medical devices from damage or contamination, and also protect persons who are storing, transporting, or using the devices from inadvertent injury. The containers can be lightweight, extremely durable, and can be opened quickly.

In some embodiments, the medical device containers are also configured to permit sterilization of medical devices which are positioned therein, and the containers can maintain these devices in a sterile environment thereafter until used.

BRIEF DESCRIPTION OF THE DRAWINGS

Specific embodiments and modifications thereof will become apparent to those skilled in the art from the examples provided in the detailed description herein having reference to the figures that follow, of which:

FIG. 4 is a cross-sectional schematic side elevation view of the base of FIG. 3 taken at line 4-4.

FIG. 5 is a cross-sectional schematic side elevation view of the base of FIG. 4 taken at line 5-5.

FIG. 6 is an enlarged schematic side elevation view of a cap of the container of FIG. 1.

FIG. 7 is a cross-sectional schematic side elevation view of the cap of FIG. 6 taken at line 7-7.

FIG. 8 is a schematic top perspective view of the protective case of FIG. 1 with a medical device disposed therein.

FIG. 9 is a close-up view of detail 9 of FIG. 8.

DETAILED DESCRIPTION OF SPECIFIC EMBODIMENTS

Examples of protective containers for sterilizing, storing and transporting needles and catheters are described herein. None of these examples should be understood to limit the inventions recited in the claims. None of the structures, steps, or other features disclosed herein are essential or indispensible; any can be omitted in some embodiments. Some of the protective containers disclosed herein can be particularly advantageous for use in rugged and abusive combat or military environments, and also can allow inexpensive and effective sterilization techniques.

Figure 1:
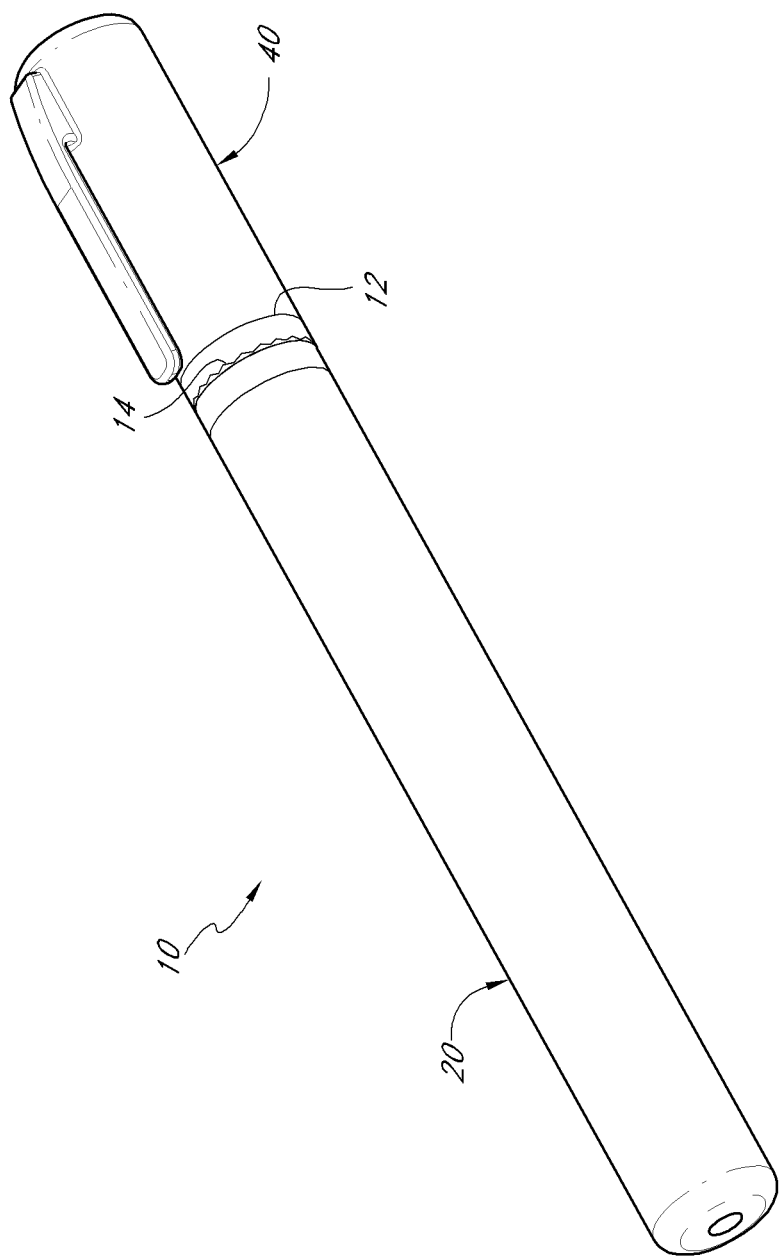
FIG. 1 is a schematic perspective view of an example of a container according to an embodiment in the present application.

In this application, the term "distal" is used to describe the direction toward the bottom of the container 10 and the term "proximal" is used to describe the direction toward the top of the container 10. In FIG. 1, the distal direction is toward the end of the container 10 with the base 20. The proximal direction is toward the end of the container 10 with the cap 40.

A protective needle container having desirable features and advantages will now be described with reference to the figures. Although the following description is provided in the context of an example of a protective needle container, the features of the present needle container can provide advantages in many other applications as well. Furthermore, although some portions of the following description is provided with reference to a needle, it is understood by one of skill in the art that the container can hold many other types of devices, such as medical devices with a catheter instead of, or in addition to, a needle. For example, in some embodiments, a needle can be disposed within a sheath of a catheter and positioned in the container. In some embodiments, the container can be configured to be used with non-medical items.

FIG. 1 illustrates an embodiment of the container 10 that includes a base 20 and a cap 40. In the illustrated embodiment, the base 20 is an elongate member with a longitudinal length sufficient to accommodate all or a portion of the length of a medical device to be stored therein, such as a needle. The cap 40 can be detachably coupled to an end of the base 20.

Figure 2:
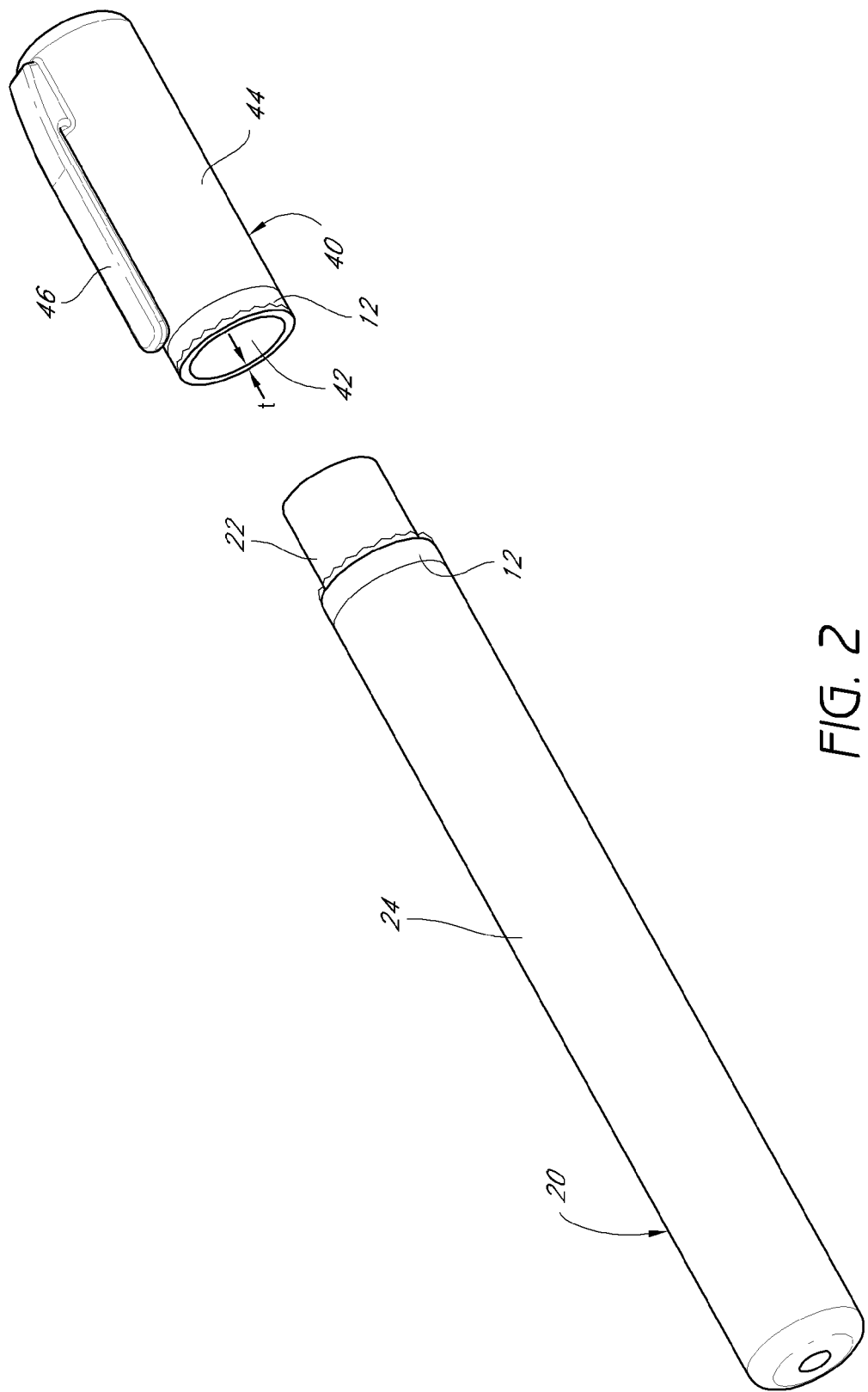
FIG. 2 is a schematic exploded perspective view of the container of FIG. 1.

In FIG. 2, the container 10 is illustrated with the cap 40 detached from the base 20. The base 20 can have a mating portion 22 that is configured to couple with the cap 40. In some embodiments, the mating portion 22 can have an outer diameter that is less than the outer diameter of the outer surface of the base 24. In some embodiments, the difference between the radius of the outer surface of the base 24 and the radius of the mating portion 22 can be substantially equal to the thickness t of the cap 40, such that the outer surface of the cap 44 is substantially flush with the outer surface of the base 24 when the cap 40 is coupled to the base 20, as illustrated in FIG. 1. A flush interface between the base 20 and cap 40 can advantageously reduce the likelihood of the container 10 becoming inadvertently caught or snagged on other objects, which can result in unintentional separation of the base 20 and cap 40. In some applications, this can be important because of the abusive conditions experienced by the container 10 and the myriad of equipment on which the container 10 can potentially become snagged.

With reference to FIG. 1, the base 20 and cap 40 can be temporarily held together by a coupling 12, such as adhesive tape, that is placed across the seam between the base 20 and cap 40. In some embodiments, the coupling 12 can have perforations 14 or a weakened portion where the coupling 12 can separate to detach the cap 40 from the base 20. The breakable coupling 12 can advantageously allow rapid deployment of the medical device by simply twisting or pulling the cap 40 from the base 20 while diminishing the risk of accidental or unintended detachment. As illustrated in FIG. 2, a broken coupling 12 can evidence when the container 10 has been used or tampered with, thus indicating that the medical device inside may no longer be sterile. Furthermore, in some embodiments the coupling 12 can be labeled or coded, such as to indicate the type of medical device contained inside. In some embodiments, the coupling 12 can indicate when the container 10 has been sterilized. For example, the coupling 12 can include a substance that changes color when it reacts with chemicals used in gas sterilization.

In some embodiments, the cap 40 and base 20 can be attached using an attachment structure, such as surfaces that produce a friction fit, as described further below. In some embodiments, the cap 40 can have threads that can engage with complementary threads on the mating portion 22. In some embodiments, the mating portion 22 can have a ridge extending around the circumference of the mating surface that fits into a depression extending around the inner surface 42 of the cap 40. In some embodiments, the mating portion 22 can have tabs, hooks, ridges, etc. that can couple with complementary features on the cap 40. In some embodiments, the base 20 can have any other attachment structure around the mating portion 22 that can interact with a complementary feature on the inner surface 42 of the cap 40. In some embodiments, the base 20 may not have a mating portion 22 and the cap 40 can couple to other portions of the base 20 through any coupling features, such as for example hooks, tabs, magnets, etc.

In some embodiments, the cap 40 can have a male portion and the base 20 can have a female portion such that the cap 40 can be inserted into the base 20 to couple the two components. The base 20 can have a cavity with an inner surface that can couple with an external surface of the cap 40.

Base

Figure 3:
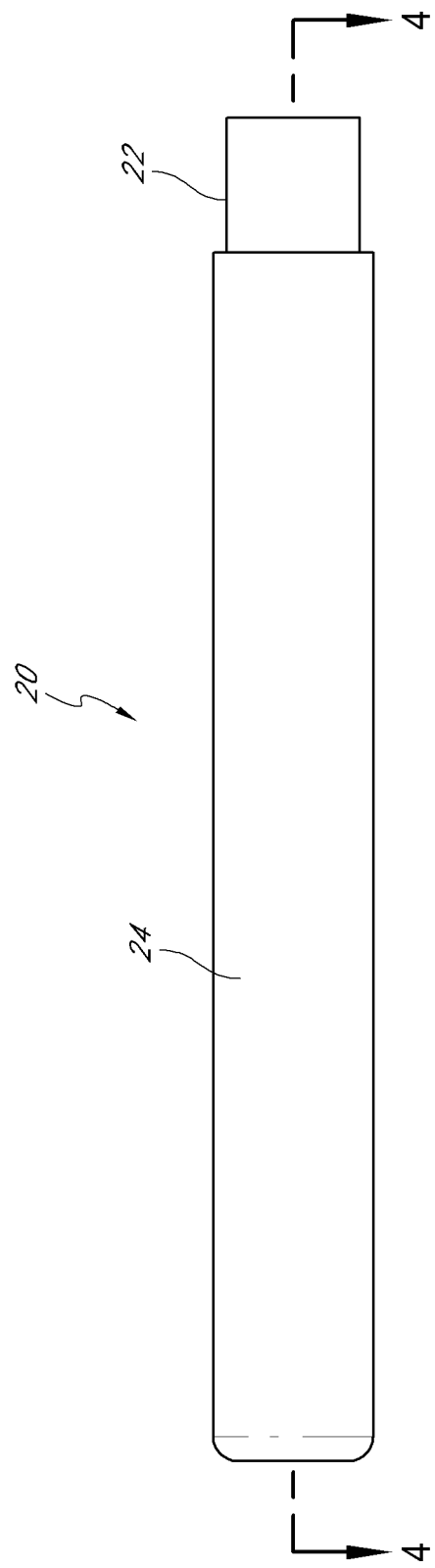
FIG. 3 is a schematic side elevation view of a base of the container of FIG. 1.

With reference to FIG. 3, the base 20 can be an elongate member with a longitudinal axis and a length sufficient to accommodate the length of a needle. In some embodiments, the base 20 can be formed in many different shapes and sizes. In some embodiments, the total length of the base 20 can be approximately 127 mm. In some embodiments, the total length of the base 20 can range from approximately 50 mm to approximately 254 mm. In other embodiments, the base 20 can be any appropriate length to accommodate an item to be contained at least partially therein.

In the illustrated embodiment, the base 20 is a generally cylindrical member. In some embodiments, the base 20 can have a generally triangular, square, polygonal or ovular cross-sectional shape. The base 20 can have any other cross-sectional shape, and the shape of the base 20 can change along its length. The outer diameter of the generally cylindrical base 20 in the illustrated embodiment is approximately 14 mm. In some embodiments, the diameter of the base 20 can range from approximately 8 mm to approximately 30 mm. In embodiments where the base 20 is not cylindrical, the provided measurements are for the transverse width, measured perpendicular to the longitudinal axis of the base 20. In some embodiments, the diameter or width can be any appropriate size to accommodate a certain category of items. In some embodiments, the base can have a width sufficient to accommodate more than one type of device, such as a plurality of needles of different sizes. For example, the base can be formed as a generally wide, flat structure with multiple cavities lined up along the width for accepting multiple needle sizes.

In some embodiments, the base 20 can have a mating portion 22 at or near the proximal end, which can couple with the cap 40. In the illustrated embodiment, the mating portion 22 has a generally cylindrical shape and a length configured to be inserted into a portion of the cap 40. In some embodiments, the mating portion 22 can have a generally triangular, square, polygonal or ovular cross-sectional shape. In other embodiments, the mating portion 22 can have any other cross-sectional shape. In some embodiments, the length of the mating portion 22 can be approximately 13 mm. In some embodiments, the length of the mating portion 22 can range from approximately 3 mm to approximately 30 mm. In other embodiments, the mating portion 22 can be longer than approximately 30 mm.

As discussed previously, in some embodiments, the mating portion 22 can have an outer diameter, or transverse width, that is less than the outer diameter of the outer surface of the base 24. In some embodiments, the diameter or width of the mating portion 22 can be approximately 12 mm. In some embodiments, the diameter or width of the mating portion 22 can range from approximately 7 mm to approximately 30 mm. In some embodiments, the mating portion 22 can have a diameter or width that increases in the distal direction to provide increasing compression forces as the base 20 and cap 40 are coupled together.

In some embodiments, the base 20 can be made of a material that can withstand the abuses and impacts associated with the rigors experienced by equipment used by military or emergency personnel. In some embodiments, the base 20 can be made of a rigid material that substantially resists bending to protect the needle contained within. In some embodiments, the material can also be generally crush resistant such that the contents are protected from impacts and compression forces that may ordinarily be encountered by persons who are storing, transporting, or using medical devices in urgent circumstances. In some embodiments, the material is impervious or substantially impervious to most or generally all gaseous, liquid or solid contaminants. In some embodiments, the material can be malleable in a forming stage for ease of manufacturing, through processes such as molding, vacuum forming, machining, etc. Some examples of suitable materials include, but are not limited to, plastics, metals, fiberglass and composites. For example, in some embodiments, the base 20 can be made of high density polyethylene plastic.

Figure 10:
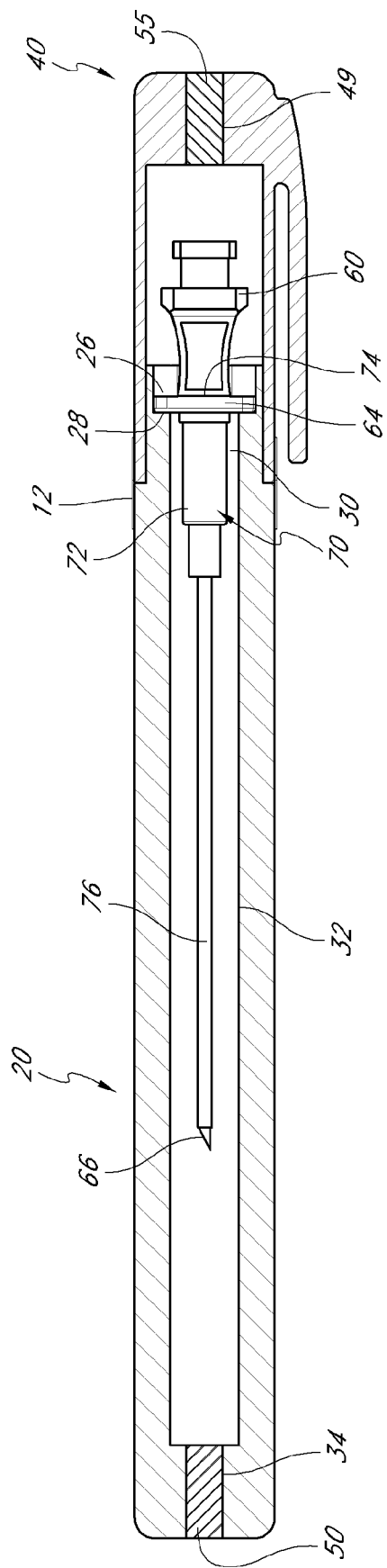
FIG. 10 is a cross-sectional schematic side elevation view of the container of FIG. 8 taken along line 10-10.

FIGS. 4 and 5 illustrate cross-sectional views of the base 20. FIG. 4 illustrates a cross-section taken at line 4-4 in FIG. 3. FIG. 5 illustrates a cross-section taken at line 5-5 in FIG. 4. FIG. 10 also illustrates, inter alia, a cross-sectional view of the base 20, cap 40, as well as a schematic of an example of a needle 60 and catheter 70.

As illustrated in the cross-sectional views, the base 20 can have a first containing region, such as a flange region 26 at or near the proximal end of the base 20. The flange region 26 can comprise a cavity with a shape substantially corresponding to the shape of at least a portion of a device to be container therein. For example, the flange region 26 can be adapted to receive a flange on a needle hub 62 and/or catheter hub 72. The flange region 26 can accept the flanges to securely retain the needle within the base 20, as described in more detail herein.

Extending distally from the distal end of the flange region 26 can be a second containing region with the container 10, such as a hub cavity 30. The first and second containing regions can have different cross-sectional diameters or widths to accommodate or engage with different portion of items to be container therein. In some embodiments, the hub cavity 30 can be configured to accommodate the needle hub 62 and/or catheter hub 72. In some embodiments, the length of the hub cavity 30 can be approximately 20 mm. In some embodiments, the hub cavity 30 can have a clearance region between with the needle hub 62 and/or catheter hub 72 and the inner wall of the container 10, such that the sides of the hubs do not contact the sides of the hub cavity 30 when the needle is properly coupled to the base 20 during storage or transportation. In some embodiments, the hub cavity 30 can be a generally cylindrical cavity having a diameter of approximately 5.5 mm. In some embodiments, the hub cavity 30 can have a diameter ranging from about 4 mm to about 30 mm.

In some embodiments, the hub cavity 30 can have a non-circular shape, such as for example a rectangular, square, ovular or polygonal cross-section. In some embodiments, the hub cavity 30 can have any shape that is configured to accept the shape of the needle hub 62 and/or catheter hub 72.

In some embodiments, the hub cavity 30 can have a close fit or interference fit with a portion of the item contained therein, such as the needle hub 62 and/or catheter hub 72, to provide generally rigid retention of at least a portion of the device while permitting another portion of the device (which may be more fragile) to be positioned more loosely within the container 10. This configuration can help prevent forces applied on the exterior of the container 10 from being transferred indirectly to the needle in a damaging way, causing the needle to be jostled excessively within the base 20 during transport of the container 10. In some embodiments, the hub cavity 30 can have a generally frustoconical shape where the diameter of the hub cavity 30 decreases in the distal direction such that the needle hub 62 and/or catheter hub 72 can be gripped tighter as it advances distally into the hub cavity 30. Similarly, in some embodiments, the hub cavity can have walls that are tapered such that the distance between the walls decreases in the distal direction to provide a progressively tighter grip as the needle hub 62 and/or catheter hub 72 is advanced distally.

Extending from the distal end of the hub cavity 30 can be a tube cavity 32 for accommodating the elongate needle tube 66 and/or catheter tube 76. The tube cavity 32 can have a length that is longer than the length of the items to be retained therein, such as the needle tube 66 and/or catheter tube 76. In some embodiments, the tube cavity 32 can be approximately 60 mm in length. In some embodiments, the tube cavity 32 can have a clearance fit with the needle tube 66 and/or catheter tube 76, such that the sides of the needle tube 66 and/or catheter tube 76 do not contact the sides of the tube cavity 32 when the needle is properly coupled to the base 20. In some embodiments, the tube cavity 32 can be a cylindrical cavity having a diameter of approximately 3 mm. In some embodiments, the tube cavity 32 can have a diameter ranging from about 1.5 mm to about 30 mm. In some embodiments, the tube cavity 32 can be the same size as the hub cavity 30 such that the tube cavity 32 and the hub cavity 30 are a single continuous cavity, which can advantageously improve ease of manufacturing. The base 20 can be formed as a single, continuous, unitary body, as illustrated, or the base 20 can be formed of multiple components.

In some embodiments, the tube cavity 32 can have a non-circular shape, such as for example a rectangular, square, ovular or polygonal cross-section. In some embodiments, the tube cavity 32 can have any shape that can accommodate the shape of the needle tube 66 and/or catheter tube 76.

In some embodiments, the tube cavity 32 can have a structure or insert that can provide support for the needle tube 66 and/or catheter tube 76. In some embodiments, the structure can be coupled toward the distal end of the needle tube 66 and/or catheter tube 76. In some embodiments the structure can be disposed around the distal tip of the needle tube 66 and/or catheter tube 76 to protect the tips from damage. In some embodiments, the structure can be a resilient material, such as rubber or foam that can absorb shocks and stresses. In some embodiments, the insert can be secured to the tube cavity 32 so that it does not slide out of the base 20 when the needle is removed. In some embodiments, an interior region of the base 20 can include additional sterilizing means, such as a resilient material with an antimicrobial agent.

Base Plug

With continued reference to FIG. 4, the base 20 can have a base plug 50 at a distal end of the base 20. The base plug 50 is configured to be inserted into the stem cavity of the base 34 and obstruct the distal end of the base 20. In some embodiments, the base plug 50 has a shape that is complementary to the shape of the stem cavity of the base 34. In the illustrated embodiment, the stem cavity of the base 34 and the base plug 50 have generally cylindrical shapes. In some embodiments, the stem cavity of the base 34 and base plug 50 can have other shapes, such as elongate shapes with square, rectangular, ovular or polygonal cross-sections. In some embodiments, the diameter or transverse width of the base plug 50 can have a size that is slightly larger than the diameter or transverse width of the stem cavity of the base 34, so that there is advantageously an interference fit between the base plug 50 and the stem cavity of the base 34. The interference fit can substantially prevent contaminants or unwanted substances from leaking past the base plug 50 into the tube cavity of the base 32. In some embodiments, the diameter of the base plug 50 can be approximately 3.5 mm, and can range from approximately 1.5 mm to approximately 12 mm. The diameter of the stem cavity of the base 34 can be approximately 3 mm, and can range from approximately 1 mm to approximately 11 mm. In some embodiments, the diameter of the stem cavity of the base 34 and the base plug 50 can have any complementary dimensions. In some embodiments, the base plug 50 can have a clearance or close fit with the stem cavity 34.

The distal surface of the base plug 50 can be generally flush with the distal surface of the base 20 for an integrated appearance. As discussed previously, a generally flush surface advantageously reduces the likelihood that the container 10 may become inadvertently caught or snagged on other objects. In some embodiments, the length of the base plug 50 can be approximately 9.5 mm, and can range from approximately 1.5 mm to approximately 20 mm. The length of the stem cavity of the base 34 can be approximately 6 mm, and can range from approximately 1.5 mm to approximately 20 mm. In some embodiments, the length of the base plug 50 and the stem cavity of the base 34 can have any other dimensions appropriate for this application.

In some embodiments, the base plug 50 is made of a material that is permeable to at least certain types of gases, but not permeable to many types of liquids and solids that are typically encountered in the intended environment of use. For example, the base plug 50 can be made of a foam material that is permeable to gases used to sterilize medical devices. In some embodiments, the foam material can be generally rigid, and in some embodiments, the foam material can be a resilient material that can be deformed and then can rebound to its original shape. In some embodiments, the base plug 50 can be made of a material with tiny pores that allow gases to pass through the material, but prevent or substantially prevent liquids and solids from passing through the material. Some examples of suitable materials include synthetic fiber materials, such as Tyvek® material.

An advantage of having a base plug 50 made of a material that is gas permeable is that the container can be gas sterilized during manufacturing using chemicals, such as ethylene oxide. For example, the assembled container 10 with the base 20, cap 40 and needle 60 can be placed in a Chemiclav until the chemical gases penetrate through one or more of the gas-permeable plugs into the cavity of the container 10 and sterilize the needle 60. In some embodiments, the gas passes through one plug, then through all or substantially all of the cavity within the container 10, and then through another plug to exit out of the container. In some embodiments, multiple containers 10 can be sterilized at the same time in the gas sterilization chamber, which can advantageously increase sterilization throughput and reduce costs. The sterilized container 10 and item therein can be stored, transported, and used in the field without additional processing or packaging, which reduces the complexity and cost of sterilizing the packaging and items therein.

Cap

FIG. 6 illustrates an embodiment of a cap 40 that can couple with the base 20. In some embodiments, the cap 40 can couple with the mating portion 22 of the base 20. The cap 40 can have a similar shape and size as the base 20, wherein the outer surface of the cap 44 can be substantially flush with the outer surface of the base 24 when the cap 40 is coupled to the base 20, as described above. In some embodiments, the diameter or transverse width of the cap 40 can be approximately 14 mm. In some embodiments, the diameter of the cap 40 can range from approximately 8 mm to approximately 30 mm.

In some embodiments, the cap 40 can be larger in diameter, or transverse width, than the base 20, in which case the outer surface of the cap 44 need not be flush with the outer surface of the base 24. However, in some embodiments, the distal end of the cap 40 can be tapered inward to form a gradual transition from the outer surface of the base 24 to the larger outer surface of the cap 44. This can advantageously help prevent snagging or catching of the container 10 on other objects.

With reference to FIG. 7, the cap 40 can have a cap cavity 48 for accepting the mating portion 22 of the base 20. The cap cavity 48 can have an inner surface 42. In some embodiments, the diameter or transverse width of the cap cavity 48 can be approximately 12 mm. In some embodiments, the diameter or transverse width of the cap cavity 48 can range from approximately 7 mm to approximately 30 mm.

In some embodiments, at least a portion of the distal end of the inner surface 42 can have a structure, such as threads or ridges, which can engage with a complementary structure on the mating portion 22 of the base 20. In some embodiments, the structures can be configured for quick release, such as by a quarter or half-turn. In some embodiments, the structures can be configured to require a longitudinal compression force before the cap 40 can be released, similar to tamper-proof medicine bottles, in order to prevent inadvertent detachment of the cap 40.

In the illustrated embodiments, there is a friction fit between the mating portion 22 and the inner surface 42. The diameter or width of the mating portion 22 can be slightly greater than the diameter or width of the inner surface 42. When the inner surface 42 is coupled to the mating portion 22, a compression force exists between the inner surface 42 and the mating portion 22 resulting from the size difference, which increases the friction between the surfaces. This friction fit can secure the cap 40 to the base 20. In some embodiments, the surface of the mating portion 22 and/or inner surface 42 can have a textured, ribbed or grooved surface to enhance the retention of the cap 40 to the base 20. For example, the mating portion 22 can have circumferential ridges around its surface to impede sliding motion of the inner surface 42 in the axial direction. Alternatively, or in addition, the inner surface 42 can have circumferential ridges around its surface.

In some embodiments, the inner surface 42 can have a tapered shape wherein the diameter or width of the inner surface 42 toward the distal end is larger than the diameter or width of the inner surface 42 at the proximal end. As the mating portion 22 is inserted proximally into the cap 40, the tapered shape of the cap cavity 48 increases the compression force between the mating portion 22 and cap 40. In some embodiments, the mating portion 22 can have a diameter or width that increases in the distal direction, to similarly provide increasing compression forces as the base 20 and cap 40 are coupled.

In some embodiments, a compressible member, made of a material such as rubber, plastic, or other pliable or elastomeric material can be attached to the base 20 and/or cap 40 to obstruct or substantially obstruct contaminants from entering the container through the interface between the base 20 and cap 40. For example, an o-ring can be positioned between the inner surface 42 and the mating portion 22. The o-ring can create a seal to prevent or substantially prevent contaminants from passing through the junction between the base 20 and cap 40. In some embodiments, the compressible member can be a resilient material that can conform to the surfaces of the mating portion 22 and inner surface 42, such as rubber or polyurethane. In some embodiments, the compressible member can have a shape other than an o-ring, such as a tubular sleeve or a circumferential flange.

As illustrated in FIGS. 6 and 7, an attachment structure, such as a clip 46 can be disposed on the outer surface of the cap 40. The clip 46 can be used to secure the container 10 to other objects, such as MOLLE gear on soldiers' equipment. The clip 46 can be a projection that extends generally parallel to the longitudinal axis of the cap 40. In the illustrated embodiment, the clip 46 extends beyond the distal end of the cap 40. In some embodiments, the length of the clip 46 can be shorter or longer. In some embodiments, the clip 46 can be integrally formed on the container 10. In some embodiments, the clip 46 can be a separate member that can be attached to the container 10. In the illustrated embodiments, the clip 46 is attached to the cap 40. However, in some embodiments, the clip 46 can be attached to the base 20. In some embodiments, the clip 46 can be other attachment devices, such as for example straps, MOLLE clips or ALICE clips. The clip 46 can be made of a resilient, yet generally rigid material, such as for example spring steel, plastics or composites. In embodiments where the clip 46 is integrally formed on the container 10, the clip 46 can be made of the same material as the container 10.

Similar to the base 20, the cap 40 can be made of a material that can withstand the abuses and impacts typically associated with medical personnel in combat environments. In some embodiments, the cap 40 can be made of a rigid material that substantially resists bending. In some embodiments, the material can be generally crush resistant to protect the needle from impacts and compression forces. In some embodiments, the material can be impervious or substantially impervious to gaseous, liquid or solid contaminants. In some embodiments, the material can be malleable for ease of manufacturing, through processes such as molding, vacuum forming, machining, etc. Some examples of such materials include, but are not limited to plastics, fiberglass and composites.

Cap Plug

At or near the proximal end of the cover 40 can be a cap plug 55, similar to the base plug 50 at the distal end of the base 20, as illustrated in FIG. 7.

The cap plug 55 is configured to be inserted into the stem cavity 49 of the cap 40 and obstruct the proximal end of the cap 40 from contaminants. In some embodiments, the cap plug 55 has a shape that is complementary to the shape of the stem cavity 49. In the illustrated embodiment, the stem cavity 49 and the cap plug 55 have generally cylindrical shapes. In some embodiments, the stem cavity 49 and cap plug 55 can have other shapes, such as elongate shapes with square, rectangular, ovular or polygonal cross-sections. In some embodiments, the diameter or transverse width of the cap plug 55 can have a size that is larger than the diameter or width of the stem cavity 49 so that there is advantageously an interference fit between the cap plug 55 and the stem cavity 49. The interference fit can prevent or substantially prevent contaminants and unwanted substances from slipping past the cap plug 55 into the cap 40. In some embodiments, the diameter of the cap plug 55 can be approximately 3.5 mm, and can range from approximately 1.5 mm to approximately 12 mm. The diameter of the stem cavity 49 can be approximately 3 mm, and can range from approximately 1 mm to approximately 11 mm. In some embodiments, the diameter of the stem cavity 49 and the cap plug 55 can be any other dimension. In some embodiments, the cap plug 55 can have a clearance or close fit with the stem cavity 49. Either or both of the plugs 50, 55 can be permanently or removably secured to the container 10 in any additional or alternative ways, such as with glue, screw threads, etc.

The proximal surface of the cap plug 55 can be generally flush with the proximal surface of the cap 40 for an integrated appearance. As discussed previously, a generally flush surface advantageously reduces the likelihood that the container 10 may become inadvertently caught or snagged on other objects. In some embodiments, the length of the cap plug 55 can be approximately 1.5 mm and range from approximately 1 mm to approximately 10 mm. The length of the stem cavity of the cap 49 can be approximately 4 mm, and can range from approximately 1 mm to approximately 10 mm. In some embodiments, the cap plug 55 can be made of a material that is the same as or generally similar to the material of the base plug 50. By providing gas-permeable plugs on both sides of the container 10, sterilizing gas can pass through substantially the entire interior of the container, or at least substantially the entire interior portion of the container that contains or comes into contact with medical devices contained therein.

In some embodiments, the base plug 50 and/or cap plug 55 can be removably attached. The plugs 50, 55 can be replaced to suit a particular situation or to exchange contaminated plugs. For example, in situations where there is a threat of chemical or biological weapons, the gas permeable plugs can be exchanged for sealed plugs that are impermeable to gases, such as rubber plugs. In another example, the plugs can be exchanged for new clean plugs when the old plugs become soiled or contaminated.

In some embodiments, the plugs 50, 55 can be removed by pulling the plugs out of the stem cavities 34, 49. In some embodiments, the plugs 50, 55 can have circumferential ridges that can engage with the stem cavities 34, 49 to provide a more secure hold on the base 20 and cap 40. In some embodiments, the plugs 50, 55 can have threads that can engage with threads in the stem cavities 34, 49, in which case the plugs can be rotated to remove the plugs 50, 55. In some embodiments, the plugs 50, 55 can have other attachment features known to those of skill in the art for securing to the base 20 and cap 40. In some embodiments, the container 10 can include more than two plugs positioned at various points therein.

Interior Fit

As illustrated in FIGS. 8-10, the device to be inserted and stored in the container 10, such as a needle 60 and/or catheter 70, can be inserted into the base 20. The flange region 26 on the base 20 can accept a needle hub flange 64 and/or catheter hub flange 74 to securely retain the needle 60 and/or catheter 70 within the base 20. The flange region 26 can include one or more cavities having shapes substantially corresponding to the shapes of the needle hub flange 64 and/or catheter hub flange 74. In the illustrated embodiment of FIG. 9, the flange region 26 has a portion with a shape that can accept the substantially circular catheter hub flange 74 and a portion with a shape that can accept the rectangular needle hub flange 64. In some embodiments, the flange region 26 can have an interference fit with needle hub flange 64 and/or catheter hub flange 74 to provide secure retention of the needle 60 and/or catheter 70. In some embodiments, the flange region 26 can have a clearance fit with the needle hub flange 64 and/or catheter hub flange 74. In some embodiments, a retention mechanism, such as a tab, hook, adhesive, or a resilient member can be disposed within or near the flange region 26 to secure the needle 60 and/or catheter 70 to the base 20.

In some embodiments, the container 10 can accept a 14-gauge needle and catheter. The 14-gauge needle and catheter can be used to prepare intravenous flow of medicines or other solutions. The 14-gauge needle can also advantageously be used as a decompression hypodermic needle that can be inserted in a patient's chest to treat tension pneumothorax. Needle decompression with a 14-gauge needle has been shown to be as successful as a chest tube in treating tension pneumothorax, while being easier to perform in the field. In some embodiments, the size of the needle can be any other size used by medical personnel. In some embodiments, the length of the needle can be approximately 3.25 inches. In other embodiments, the length of the needle can be any length suitable for a situation.

In some embodiments, the distal surface 28 of the flange region 26 can have a substantially flat surface that is substantially perpendicular to the longitudinal axis of the base 20. The substantially flat surface can aid the inserted needle 60 and/or catheter 70 to properly align within the base 20 by seating the needle hub flange 64 and/or catheter hub flange 74 substantially flush or flush with the distal surface 28, as illustrated in FIG. 10. In some embodiments, the distal surface 28 can have a configuration or texture that is complementary with a mating surface of the needle hub flange 64 and/or catheter hub flange 74, such that the needle tube 66 and/or catheter tube 76 are oriented substantially parallel to the longitudinal axis of the base 20 when the needle 60 and/or catheter 70 is inserted in the base 20. In some embodiments, the distal surface 28 can have a retention feature, such as adhesive or Velcro® that can help secure the needle 60 and/or catheter 70 to the base 20. In some embodiments, the flange region 26 can align the needle 60 and/or catheter 70 so that the needle tube 66 and/or catheter tube 76 do not contact the sides of the tube cavity 32.

In some embodiments, the flange region 26 can firmly hold the needle hub flange 64 and/or catheter hub flange 74 within the base 20 so that the needle 60 and/or catheter 70 is not damaged inside of the container 10 during transport. For example, the needle hub flange 64 and/or catheter hub flange 74 can have a close fit or interference fit with the flange region 26, which can result in substantially rigid retention of the needle 60 and/or catheter 70. However, the fit of the needle hub flange 64 and/or catheter hub flange 74 is not so tight that the catheter 70 separates from the needle 60 and remains caught in the flange region 26 when the needle 60 is pulled out of the base 20. The fit between the needle hub flange 64 and/or catheter hub flange 74 and the flange region 26 can be configured to provide sufficient support to firmly hold the needle 60 and/or 70 in the base 20, yet the fit can be loose enough so that the catheter hub flange 74 separates from the flange region 26 when the needle 60 is pulled out with ordinary manual force.

As illustrated in FIG. 10, the hub cavity 30 can be configured to accept the needle hub 62 and/or catheter hub 72. As described previously, and as illustrated in FIG. 10, in some embodiments the hub cavity 30 can have a clearance fit with the needle hub 62 and/or catheter hub 72, wherein the sides of the needle hub 62 and/or catheter hub 72 do not contact the sides of the hub cavity 30 when the needle 60 and/or catheter 70 is properly coupled to the base 20. In some embodiments, the hub cavity 30 can have a close fit or interference fit with the needle hub 62 and/or catheter hub 72 to provide firm retention of the needle 60 and/or catheter 70. The close or interference fit can help prevent the needle 60 and/or catheter 70 from being jostled within the base 20 during transport of the container 10.

The needle tube 66 and/or catheter tube 76 can be contained in the tube cavity 32. In some embodiments, the tube cavity 32 can have a clearance fit with the needle tube 66 and/or catheter tube 76, such that the sides of the needle tube 66 and/or catheter tube 76 do not contact the sides of the tube cavity 32 when the needle 60 and/or catheter 70 is properly coupled to the base 20. In some embodiments, there is sufficient clearance so that the needle tube 66 and/or catheter tube 76 do not contact the wall of the tube cavity 32 when the container 10 experiences vibrations or impacts. For additional support, in some embodiments, the tube cavity 32 can have a structure or insert to support the end of the needle tube 66 and/or catheter tube 76, as described above. Although it can be advantageous for the needle tube 66 and/or catheter tube 76 to generally avoid contact with the sides of the tube cavity 32, or to limit or obstruct contact the sides of the tube cavity 32, in some embodiments, the sides of the needle tube 66 and/or catheter tube 76 can be permitted to contact the sides of the tube cavity 32.

The container 10 can have features that advantageously make it easy to use and quickly deployable. In some embodiments, the container 10 can be color coded to identify the type and size of the needle contained inside. The color codes can help a medic quickly find and identify the necessary needles in an overstuffed medic bag. The container 10 can be sized and shaped to be easily gripped by medic personnel, even while wearing gloves. In some embodiments, the container 10 can have features to enhance gripping of the components, such as ridges, rubber covers, or textured surfaces.

Furthermore, the container 10 can be designed for improved deployment of the needle 60 and/or catheter 70. As illustrated in FIG. 8, the needle hub 62 can extend out of the base 20 and can be easily grasped by the medic. The needle 60 and/or catheter 70 can then be removed from the base 20 and inserted into the patient without having to reposition the grip or touch other parts of the needle 60 and/or catheter 70. Thus, the chances of contaminating the needle tub 66 and/or catheter tube 76 can be minimized.

The reference numbers described in the following embodiments are designated with primes ('), which label parts that can be similar to the parts with corresponding reference numbers without primes.

Figure 11:
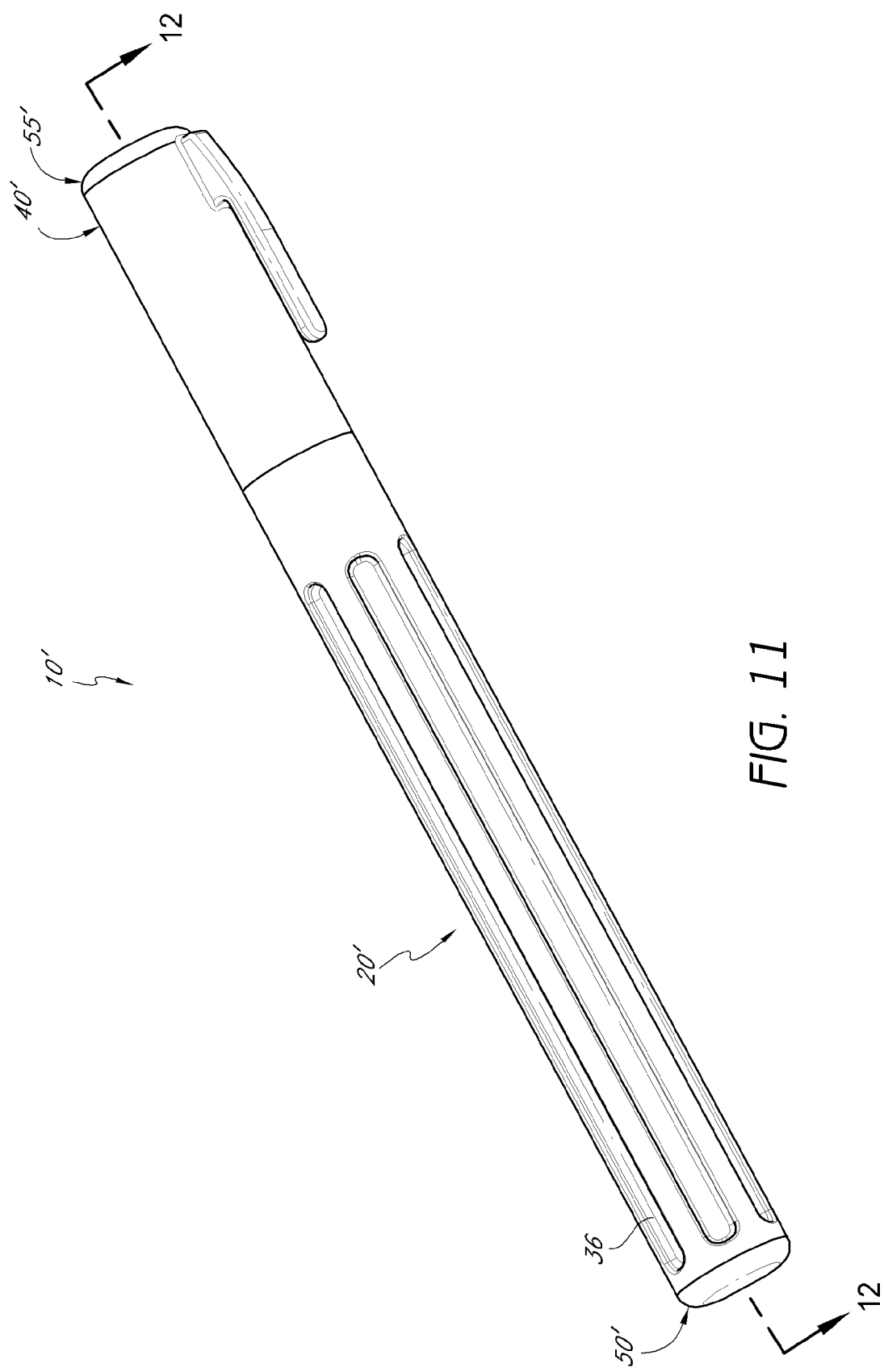
FIG. 11 is a schematic perspective view of a container according to another embodiment in the present application.

FIG. 11 illustrates an alternate embodiment of a container 10' having channels 36 extending longitudinally along the length of the base 20'. The illustrated embodiments includes six channels, however other embodiments can have more or less channels 36. The channels 36 can provide structural rigidity and strength. Alternatively, the base 20' can have ridges for added structural rigidity and strength.

Figure 12:
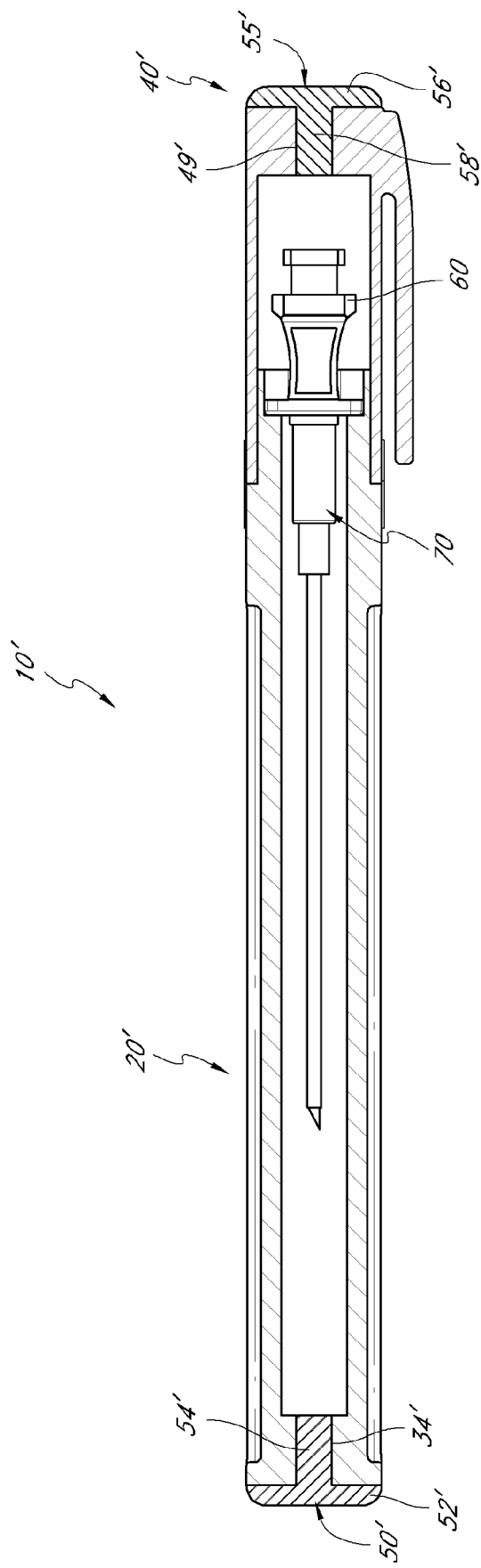
FIG. 12 is a cross-sectional schematic side elevation view of the container of FIG. 11 taken along line 12-12.
Figure 13:
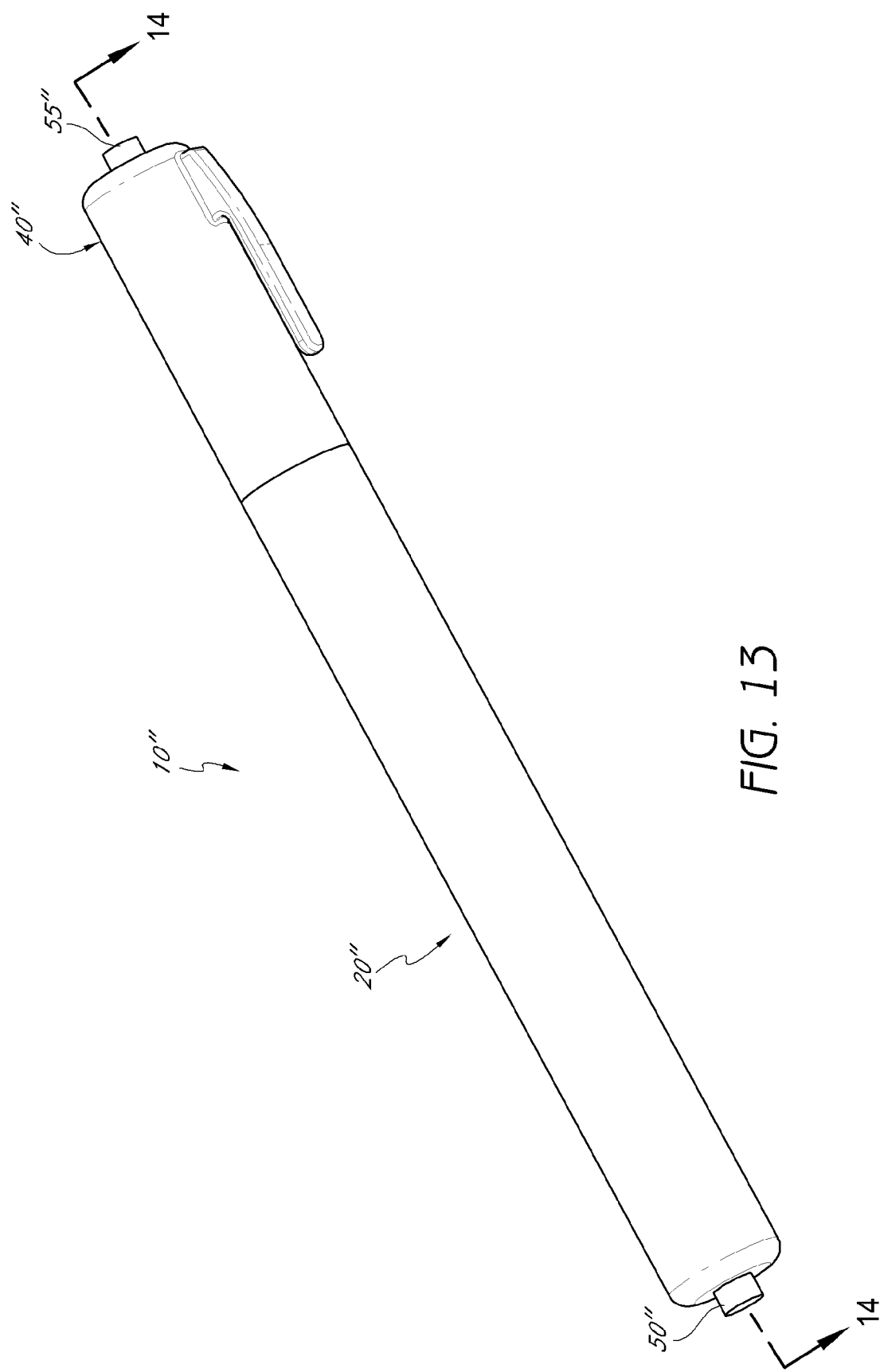
FIG. 13 is a schematic top perspective view of a container according to another embodiment in the present application.

With reference to FIGS. 11 and 12, the base plug 50' can have a bottom portion 52' and a stem portion 54'. In the illustrated embodiment, the base plug 50' has a bottom portion 52 that has generally the same shape and diameter as the adjacent end of the body 20' for an integrated appearance and generally flush fit with the outer surface of the base 24'. As discussed previously, a generally flush interface advantageously reduces the likelihood that the container 10' may become inadvertently caught or snagged on other objects. In some embodiments, the bottom portion can have a shape that is not integral with the shape of the base. For example, FIG. 13 illustrates a base plug 50" having a bottom portion that is a generally cylindrical shape with a diameter that is smaller than the diameter of the base 20". In other embodiments, the top portion of the plug can have any other shape.

With continued reference to FIG. 12, the stem portion 54' of the base plug 50' is configured to be inserted into the stem cavity of the base 34' and obstruct the distal end of the base 20. In some embodiments, the stem portion 54' has a shape that is complementary to the shape of the stem cavity of the base 34'. In the illustrated embodiment, the stem cavity of the base 34' and the stem portion 54 have generally cylindrical shapes. In some embodiments, the stem cavity of the base 34' and stem portion 54' can have other shapes, such as elongate shapes with square, rectangular, ovular or polygonal cross-sections. In some embodiments, the diameter or transverse width of the stem portion 54' can have a size that is slightly larger than the diameter or transverse width of the stem cavity of the base 34', so that there is advantageously an interference fit between the stem portion 54' and the stem cavity of the base 34'. The interference fit can substantially prevent contaminants or unwanted substances from leaking past the base plug 50' into the tube cavity of the base. In some embodiments, the diameter of the stem cavity of the base 34' and the stem portion 54' can have any complementary dimensions. In some embodiments, the stem portion 54' can have a clearance or close fit with the stem cavity 34'.

At or near the proximal end of the cover 40' can be a cap plug 55', similar to the base plug 50' at the distal end of the base 20'. As illustrated in FIG. 12, the cap plug 55' can have a top portion 56' and a stem portion 58'. The illustrated embodiment of the cap plug 55' has a top portion 56' that has generally the same shape and diameter as the proximal end of the cap 40' for an integrated appearance and generally flush fit with the outer surface of the cap 44. As discussed previously, a generally flush interface advantageously reduces the likelihood that the container 10 might become inadvertently caught or snagged on other objects. In some embodiments, the top portion can have a shape that is not integral with the shape of the base, as described above and as illustrated for example in FIG. 13. In other embodiments, the top portion of the cap plug can have other shapes.

The stem portion of the cap plug 58' is configured to be inserted into the stem cavity 49' of the cap 40' and obstruct the proximal end of the cap 40' from contaminants. In some embodiments, the stem portion 58' has a shape that is complementary to the shape of the stem cavity 49'. In the illustrated embodiment, the stem cavity 49' and the stem portion 58' have generally cylindrical shapes. In some embodiments, the stem cavity 49' and stem portion 58' can have other shapes, such as elongate shapes with square, rectangular, ovular or polygonal cross-sections. In some embodiments, the diameter or transverse width of the stem portion 58' can have a size that is larger than the diameter or width of the stem cavity 49' so that there is advantageously an interference fit between the stem portion 58' and the stem cavity 49'. The interference fit can prevent or substantially prevent contaminants and unwanted substances from slipping past the cap plug 55' into the cap 40'. In some embodiments, the stem portion 58' can have a clearance or close fit with the stem cavity 49'. Either or both of the plugs 50', 55' can be permanently or removably secured to the container 10' in any additional or alternative ways, such as with glue, screw threads, etc.

Figure 14:
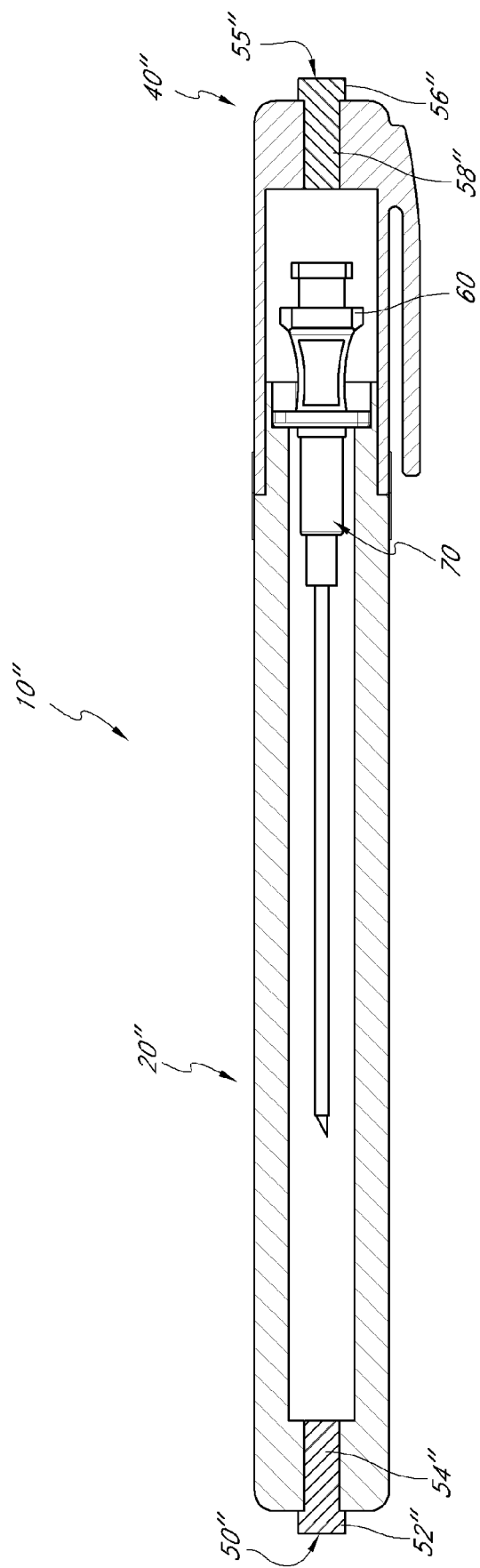
FIG. 14 is a cross-sectional schematic side elevation view of the container of FIG. 11 taken along line 14-14.

FIGS. 13 and 14 illustrate another embodiment of a container 10" having a base plug 50" and cap plug 55" that is not integrally contoured with the shape of the base 20" and cap 40". As illustrated in FIG. 14, the diameter of the bottom portion 52" of the base plug 50" is smaller than the diameter of the base 20" and the diameter of the top portion 56" of the cap plug 55" is smaller than the diameter of the cap 40". In some embodiments, this configuration of the plugs 50", 55" advantageously promotes easier grasping and exchange of the plugs.

Although certain embodiments, features, and examples have been described herein, it will be understood by those skilled in the art that many aspects of the methods and devices illustrated and described in the present disclosure may be differently combined and/or modified to form still further embodiments. For example, any one component of the protective containers illustrated and described above can be used alone or with other components without departing from the spirit of the present invention. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present invention. Thus, it is intended that the scope of the present invention should not be limited by the particular embodiments described above, but should be determined only by a fair reading of the claims that follow.

The following is claimed:

1. A needle or catheter container comprising:
   a base comprising a cavity open toward a proximal end of the base, the cavity comprising a length and a width configured to substantially correspond to the shape of a medical needle or catheter, and the cavity comprising a flange receiving region recessed within an interior wall of the container and configured to accept a flange of a needle and/or catheter such that the flange receiving region securely retains the needle or catheter;
   a cap comprising a distal end configured to couple with the proximal end of the base;
   at least one plug made of a material that is gas permeable, but resists the passage of liquids and solids; and
   a needle and/or catheter comprising a flange and a hub, wherein the flange receiving region comprises a flange seat positioned at a location within the base such that, when the flange is seated in the flange receiving region, a majority of the hub that is proximal of the flange extends outside of the proximal end of the base, and wherein in a region below the flange seat of the base, a clearance region is formed between the inner wall of the base and the needle hub where no portion of the needle hub contacts the inner wall of the base.

2. The needle or catheter container of claim 1, wherein the at least one plug is made of a synthetic fiber material.

3. The needle or catheter container of claim 1, wherein the at least one plug is disposed on a distal end of the base.

4. The needle or catheter container of claim 1, wherein the at least one plug is disposed on a proximal end of the cap.

5. The needle or catheter container of claim 1, wherein the at least one plug is generally flush with a surface of the container.

6. The needle or catheter container of claim 1, wherein the flange receiving region is sized and shaped to produce an interference fit with the flange of the needle and/or catheter.

7. The needle or catheter container of claim 1, wherein at least a portion of the container is made of plastic.

8. The needle or catheter container of claim 1, further comprising an attachment device for securing to the container to other objects.

9. The needle or catheter container of claim 8, wherein the attachment device is a clip.

10. The needle or catheter container of claim 8, wherein the attachment device is a strap.

11. The needle or catheter container of claim 1, wherein the base and cap are coupled through an interference fit.

12. The needle or catheter container of claim 1, wherein the base further comprises a structure toward the proximal end that are configured to engage with a complementary structure toward the distal end of the cap.

13. The needle or catheter container of claim 1, further comprising a compressible member between the base and cap.

14. The needle or catheter container of claim 1, wherein the outer surface of the base is flush with the outer surface of the cap when assembled.

15. The needle or catheter container of claim 1, further comprising at least one depression along the longitudinal length of the base and/or cap.

16. The needle or catheter container of claim 1 in which the needle is disposed within a catheter.

17. A medical device for use in storing or transporting medical needles, the medical device comprising:
   a base configured to hold a needle, the base comprising a flange seat;
   a cap attachable to the base;

a plug made of a material that is gas permeable, but resists the passage of liquids and solids;

a needle comprising a needle hub, the needle being disposed within the flange seat of the base, the needle being sterilized by passing a sterilizing gas through the plug, wherein in a region below the flange seat of the base, a clearance region is formed between an inner wall of the base and the needle hub where no portion of the needle hub contacts the inner wall of the base.

18. The medical device of claim 17, wherein the container comprises a plurality of plugs.

19. The medical device of claim 18, wherein the needle is sterilized by passing the gas into the container by way of a first of the plurality of plugs and out of the container by way of a second of the plurality of plugs.

20. The medical device of claim 17, wherein the needle is attached within the container in a manner that generally prevents the needle tip from contacting the sides of the container.

* * * * *

UNITED STATES PATENT AND TRADEMARK OFFICE
CERTIFICATE OF CORRECTION

| | | |
|---|---|---|
| PATENT NO. | : 8,579,115 B2 | Page 1 of 1 |
| APPLICATION NO. | : 12/869614 | |
| DATED | : November 12, 2013 | |
| INVENTOR(S) | : Murphy et al. | |

It is certified that error appears in the above-identified patent and that said Letters Patent is hereby corrected as shown below:

In the Specification

In column 2 at lines 39-40, Change "indispensible;" to --indispensable;--.

In column 5 at line 16, Change "container" to --contained--.

In column 5 at line 27, Change "container" to --contained--.

Signed and Sealed this
Twenty-fourth Day of June, 2014

Michelle K. Lee
*Deputy Director of the United States Patent and Trademark Office*